US00PP37668P2

(12) United States Plant Patent
Sato

(10) Patent No.: US PP37,668 P2
(45) Date of Patent: Sep. 1, 2026

(54) ***BIDENS* PLANT NAMED 'SUNBIDEVB 8'**

(50) Latin Name: *Bidens ferulifolia*
Varietal Denomination: SUNBIDEVB 8

(71) Applicant: Kazunori Sato, Tokyo (JP)

(72) Inventor: Kazunori Sato, Tokyo (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 19/341,909

(22) Filed: Sep. 26, 2025

(51) Int. Cl.
*A01H 5/02* (2018.01)
*A01H 6/14* (2018.01)

(52) U.S. Cl.
USPC ..... Plt./410
CPC ..... *A01H 6/14* (2018.05)

(58) Field of Classification Search
USPC ..... Plt./410
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Bidens* plant named 'SUNBIDEVB 8', characterized by its compact, upright to outwardly spreading and mounding plant habit; vigorous growth habit; freely branching habit; freely flowering habit; year-round flowering habit; large inflorescences with bright yellow-colored ray florets; and good garden performance.

2 Drawing Sheets

Figure 1:
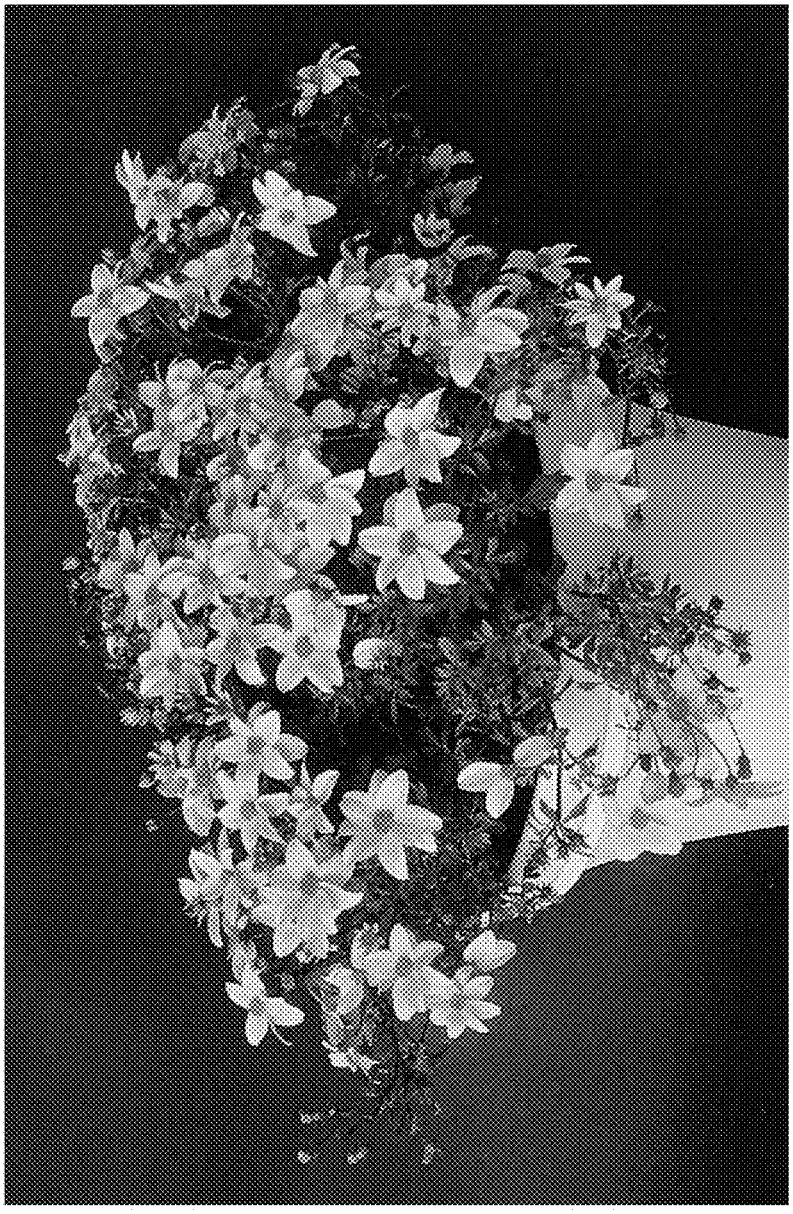

Botanical designation: *Bidens ferulifolia.*
Cultivar denomination: 'SUNBIDEVB 8'.

BACKGROUND OF THE INVENTION

The present invention relates to a new and distinct cultivar of *Bidens* plant, botanically known as *Bidens ferulifolia* and hereinafter referred to by the name 'SUNBIDEVB 8'.

The new *Bidens* plant is a product of a planned breeding program conducted by the Inventor in Fukaya, Saitama, Japan. The objective of the breeding program is to create new compact and mounding *Bidens* plants with year-round flowering habit and numerous inflorescences with yellow-colored ray florets.

The new *Bidens* plant originated from a cross-pollination made by the Inventor in Fukaya, Saitama, Japan in March, 2017 of a proprietary selection of *Bidens ferulifolia* identified as code number 912-16, not patented, as the female, or seed parent with a proprietary selection of *Bidens ferulifolia* identified as code number 201-9-26, not patented, as the male, or pollen, parent. The new *Bidens* plant was discovered and selected by the Inventor as a single flowering plant from within the progeny of the stated cross-pollination in a controlled greenhouse environment in Fukaya, Saitama, Japan in February, 2018.

Asexual reproduction of the new *Bidens* plant by vegetative cuttings in a controlled environment in Fukaya, Saitama, Japan since December, 2020 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'SUNBIDEVB 8'. These characteristics in combination distinguish 'SUNBIDEVB 8' as a new and distinct *Bidens* plant:

1. Compact, upright to outwardly spreading and mounding plant habit.
2. Vigorous growth habit.
3. Freely branching habit.
4. Freely flowering habit.
5. Year-round flowering habit.
6. Large inflorescences with bright yellow-colored ray florets.
7. Good garden performance.

Plants of the new *Bidens* differ primarily from plants of the female parent selection in the following characteristics:

1. Plants of the new *Bidens* are more mounding than and not as upright as plants of the female parent selection.
2. Plants of the new *Bidens* flower throughout the year whereas plants of the female parent selection only flower in the summer and winter.
3. Plants of the new *Bidens* have shorter peduncles than plants of the female parent selection.

Plants of the new *Bidens* differ primarily from plants of the male parent selection in the following characteristics:

1. Plants of the new *Bidens* are more mounding than and not as trailing as plants of the male parent selection.
2. Plants of the new *Bidens* flower throughout the year whereas plants of the male parent selection only flower in the summer and winter.
3. Plants of the new *Bidens* are more high temperature tolerant than plants of the male parent selection.

Plants of the new *Bidens* can be compared to plants of *Bidens ferulifolia* 'Sunbidevb 1', disclosed in U.S. Plant Pat.

No. 29,028. In side-by-side comparisons, plants of the new *Bidens* differ primarily from plants of 'Sunbidevb 1' in the following characteristics:

1. Plants of the new *Bidens* are more vigorous than plants of 'Sunbidevb 1'.
2. Plants of the new *Bidens* are more mounding than and not as upright as plants of 'Sunbidevb 1'.
3. Plants of the new *Bidens* have larger and darker green-colored leaves than plants of 'Sunbidevb 1'.
4. Plants of the new *Bidens* have larger inflorescences than plants of 'Sunbidevb 1'.
5. Plants of the new *Bidens* have shorter peduncles than plants of 'Sunbidevb 1'.

BRIEF DESCRIPTION OF THE PHOTOGRAPHS

The accompanying photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

The photograph on the first sheet (FIG. 1) is a side perspective view of a typical flowering plant of 'SUNBIDEVB 8' grown in a container.

Figure 2:
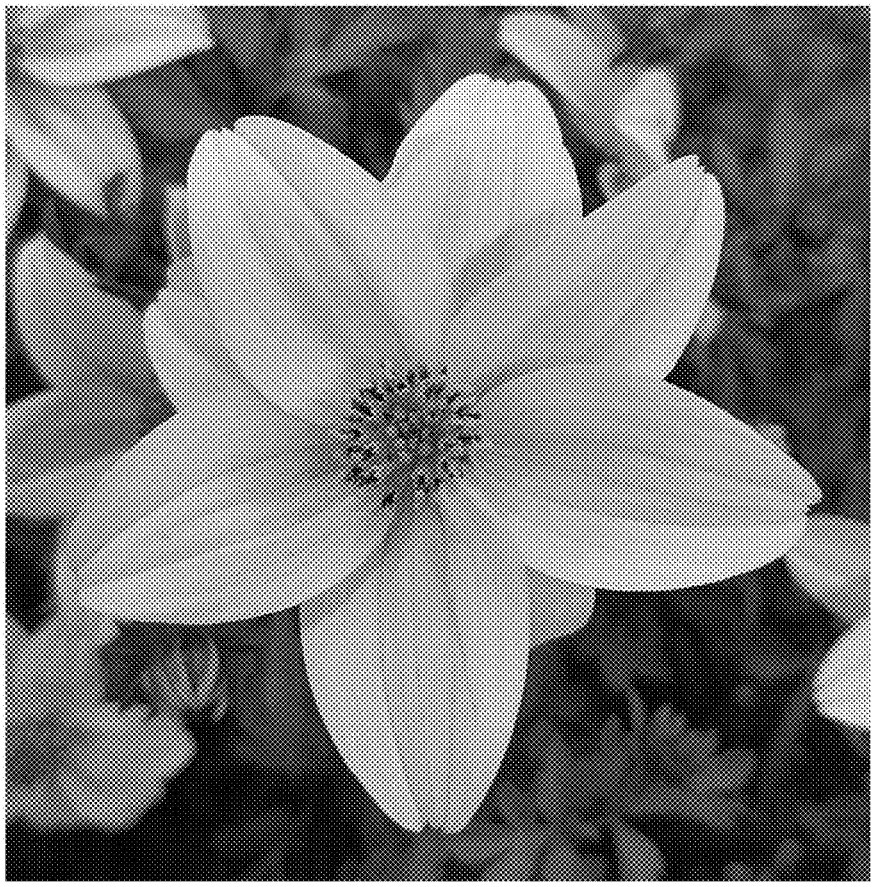

The photograph on the second sheet (FIG. 2) is a close-up view of a typical inflorescence of 'SUNBIDEVB 8'.

DETAILED BOTANICAL DESCRIPTION

The aforementioned photographs and following observations and measurements describe plants grown in 18-cm containers during the autumn in an outdoor nursery in Higashiomi, Shiga, Japan and under cultural practices typical of commercial *Bidens* production. During the production of the plants, day temperatures ranged from 20° C. to 30° C. and night temperatures ranged from 10° C. to 20° C. Plants were three months old when the photographs and description were taken. In the following description, color references are made to The Royal Horticultural Society Colour Chart, 2015 Edition, except where general terms of ordinary dictionary significance are used.

Botanical classification: *Bidens ferulifolia* 'SUNBIDEVB 8'.

parentage:

*Female, or seed, parent*.—Proprietary selection of *Bidens ferulifolia* identified as code number 912-16, not patented.

*Male, or pollen, parent*.—Proprietary selection of *Bidens ferulifolia* identified as code number 201-9-26, not patented.

Propagation:

*Type*.—By vegetative cuttings.

*Time to initiate roots, summer*.—About seven days at temperatures ranging from 20° C. to 25° C.

*Time to initiate roots, winter*.—About ten days at temperatures ranging from 12° C. to 15° C.

*Time to produce a rooted young plant, summer*.—About ten days at temperatures ranging from 20° C. to 25° C.

*Time to produce a rooted young plant, winter*.—About two weeks at temperatures ranging from 12° C. to 15° C.

*Root description*.—Fibrous; typically white in color, actual color of the roots is dependent on substrate composition, water quality, fertilizers, substrate temperature and physiological age of roots.

*Rooting habit*.—Freely branching.

Plant description:

*Plant and growth habit*.—Compact, upright to outwardly spreading and mounding plant habit; vigorous growth habit.

*Branching habit*.—Freely branching habit with about six primary lateral branches with secondary lateral branches potentially forming at every node.

*Plant height*.—About 23.5 cm.

*Plant diameter or spread*.—About 56 cm.

*Lateral branches*.—Length: About 20.6 cm. Diameter: About 2.2 mm. Internode length: About 2.3 cm. Strength: Strong. Aspect: Upright to outwardly. Texture: Mostly smooth and glabrous to sparsely pubescent. Color: Close to 137B.

Leaf description:

*Arrangement*.—Opposite, simple.

*Length*.—About 2.6 cm.

*Width*.—About 3.3 cm.

*Shape*.—Roughly deltoid; pinnatisect.

*Apex*.—Acute.

*Base*.—Truncate.

*Margin*.—Serrate.

*Texture, upper and lower surfaces*.—Mostly smooth and glabrous to sparsely pubescent.

*Venation pattern*.—Pinnate, reticulate.

*Color*.—Developing and fully expanded leaves, upper surface: Close to 137B; venation, close to 138B. Developing and fully expanded leaves, lower surface: Close to 138B; venation, close to 138B.

*Petioles*.—Length: About 4.4 mm. Diameter: About 1 mm. Texture, upper and lower surfaces: Sparsely pubescent. Color, upper and lower surfaces: Close to 138B.

Inflorescence description:

*Appearance*.—Large single inflorescences with ray and disc florets forming acropetally on a receptacle; upright inflorescences positioned above and beyond the foliar plane on strong peduncles; inflorescences face mostly upright.

*Flowering habit*.—Freely flowering habit with about 132 inflorescences developing per plant.

*Fragrance*.—Fragrant; pleasant.

*Natural flowering season*.—Plants flower year-round in Japan; early flowering habit, plants begin flowering about four weeks after planting rooted young plants.

*Inflorescence longevity*.—Individual inflorescences last about seven to ten days on the plant; inflorescences not persistent.

*Inflorescence buds*.—Height: About 1.1 cm. Diameter: About 7 mm. Shape: Ovoid. Color: Distally, close to 7A; proximally, close to 7B.

*Inflorescence size*.—Diameter: About 4.5 cm. Depth (height): About 1.3 cm. Disc diameter: About 7 mm.

*Receptacles*.—Diameter: About 3.8 mm. Height: About 1 cm. Color: Close to 144B.

*Ray florets*.—Number of ray florets per inflorescence: About eight arranged in a single whorl. Length: About 2.3 cm. Width: About 1.2 cm. Shape: Elliptic. Apex: Mostly acute to shallowly emarginate. Base: Obtuse. Margin: Entire. Aspect: Mostly flat and horizontal. Texture, upper and lower surfaces: Smooth, glabrous. Color: When opening, upper surface: Close to 7A. When opening, lower surface: Close to 7B. Fully opened, upper surface: Close to 7A; venation, close to 7A. Fully opened, lower surface: Close to 6A; venation, close to 148A.

*Disc florets*.—Number of disc florets per inflorescence: About 72. Shape: Tubular, elongated; apex, five-pointed. Length: About 5.7 mm. Diameter: About 1 mm. Texture, inner and outer surfaces: Smooth, glabrous. Color, inner and outer surfaces: Close to 153B.

*Phyllaries*.—Quantity per inflorescence: About 16. Length: About 3.4 mm. Width: About 1.2 mm. Shape: Lanceolate. Apex: Acute. Base: Truncate, fused. Margin: Entire. Texture, upper and lower surfaces: Smooth, glabrous to sparsely pubescent. Color, upper surface: Distally, close to 152B; proximally, close to 137A. Color, lower surface: Close to 137B.

*Peduncles*.—Length, terminal peduncle: About 3.5 cm. Diameter: About 1.2 mm. Strength: Strong; flexible. Aspect: Upright to outwardly, inflorescences held above and beyond the foliar plane. Texture: Smooth, glabrous. Color: Close to 137B.

*Reproductive organs*.—Androecium: Present on disc florets only. Quantity per disc floret: Five. Filament length: About 4 mm. Filament color: Close to 154C. Anther shape: Lanceolate. Anther size: About 0.6 mm by 2.4 mm. Anther color: Close to N79A. Pollen amount: Moderate. Pollen color: Close to 7A. Gynoecium: Present on ray and disc florets. Pistil length: About 6.1 mm. Style color: Close to 154B. Stigma shape: Bifurcate. Stigma color: Close to N79A. Ovary color: Close to 154B.

*Seeds*.—To date, seed development has not been observed on plants of the new *Bidens*.

Pathogen & pest resistance: To date, plants of the new *Bidens* have not been shown to be resistant to pathogens and pests common to *Bidens* plants.

Garden performance: Plants of the new *Bidens* have exhibited good garden performance and to tolerate rain, wind and temperatures ranging from 5° C. to 35° C.

It is claimed:

1. A new and distinct *Bidens* plant named 'SUNBIDEVB 8' as herein illustrated and described.

* * * * *